(12) United States Patent
Riebesehl et al.

(10) Patent No.: US 6,686,365 B2
(45) Date of Patent: Feb. 3, 2004

(54) PHARMACEUTICAL COMPOSITION

(75) Inventors: Bernd Ulrich Riebesehl, Hamburg (DE); Jens Kemken, Hamburg (DE)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/181,379

(22) PCT Filed: Jan. 23, 2001

(86) PCT No.: PCT/US01/00648

§ 371 (c)(1),
(2), (4) Date: Oct. 4, 2002

(87) PCT Pub. No.: WO01/56575

PCT Pub. Date: Aug. 9, 2001

(65) Prior Publication Data

US 2003/0212083 A1 Nov. 13, 2003

(30) Foreign Application Priority Data

Feb. 4, 2000 (GB) ............................................... 0002691
Aug. 9, 2000 (GB) ............................................... 0019599

(51) Int. Cl.$^7$ ............................................ A61K 31/505
(52) U.S. Cl. ....................................................... 514/258
(58) Field of Search .......................................... 514/258

(56) References Cited

U.S. PATENT DOCUMENTS

| | | | | |
|---|---|---|---|---|
| 5,326,759 A | * | 7/1994 | Hlavka et al. | 514/227.5 |
| 5,344,932 A | * | 9/1994 | Taylor | 544/280 |
| 2002/0010164 A1 | * | 1/2002 | Abrahamson et al. | 514/167 |

OTHER PUBLICATIONS

Teicher et al, Seminars in Oncology, vol. 25(2), pp. 55–62 (Apr. 1999).*

* cited by examiner

*Primary Examiner*—James H. Reamer
(74) *Attorney, Agent, or Firm*—Elizabeth A. McGraw; MaCharri R. Vorndran-Jones

(57) ABSTRACT

The present invention provides a pharmaceutical composition comprising pemetrexed; at least one antioxidant selected from the group consisting of monothioglycerol, L-cysteine, and thioglycolic acid; and a pharmaceutically acceptable excipient. The pharmaceutical formulation is suitable for liquid parenteral administration.

20 Claims, No Drawings

PHARMACEUTICAL COMPOSITION

The present invention relates to a liquid composition comprising the known compound pemetrexed, in particular, the present invention relates to a liquid composition comprising pemetrexed and an antioxidant; which liquid composition is stable and pharmaceutically elegant.

Certain folic acid antimetabolites are known to be antineoplastic agents. These compounds inhibit enzymatic conversion involving metabolic derivatives of folic acid. One such compound, described by U.S. Pat. No. 5,344,932, is currently being developed for potential use as a pharmaceutical agent. This compound, known as "pemetrexed", is most desirably formulated into a concentrated liquid for administration as an infusion dosage form. Pemetrexed Disodium is the active ingredient in the anticancer drug ALIMTA now in clinical development by Eli Lilly and Company.

The formulation teachings of the U.S. Pat. No. 5,344,932 provide that the compounds claimed therein can be administered parenterally.

A ready to use, stable, ready to reconstitute solution that could be stored at room temperature is particularly desired for a pharmaceutical such as pemetrexed, wherein such ready to use formulation provides easier, safer handling, storage, and distribution. It is particularly desirable if the stable formulation can be prepared without the use of freeze drying techniques. The desired liquid formulation can offer enhanced safety for caregiver handling of the cytotoxic materials. Further, a stable, ready to use formulation is more acceptable to the customer.

It was discovered that a simple, isotonic saline solution of pemetrexed is not pharmaceutically acceptable for commercial purposes due to degradation of the solution to form unacceptable related substances. It has now been discovered that pharmaceutically acceptable, concentrated, ready to use, liquid solutions of pemetrexed may be prepared when the formulation includes certain antioxidants, including monothioglycerol, L-cysteine, and thioglycolic acid. Other antioxidants were studied; however, surprisingly, of the antioxidants studied, only these provided the desired formulation characteristics described herein.

The claimed formulation exhibits acceptable stability, retains a pharmaceutically desirable appearance, maintains the desired enatiomeric stability, and fulfils the health care provider's desire for a stable, ready to use liquid formulation. Additionally, the formulation provided herein, is suitable for parenteral dosage, can be delivered to the health care provider in a clear vial and can be stored at temperatures above 4 (four) Celcius in a highly concentrated state.

The present invention addresses the need for a pharmaceutically stable liquid pemetrexed formulation having both color stability and acceptable shelf life stability with regard to retaining the solution dosage form and avoiding unacceptable degradation to undesired related substances. Additionally, the claimed formulations can be diluted to the desired administration concentration by the health care provider. Finally, the formulations provided herein do not require the addition of any preservative, other than the antioxidant, in order to retain the desired concentration and stability.

The present invention particularly provides a pharmaceutical composition comprising:

a) pemetrexed;
b) at least one antioxidant selected from the group consisting of
   i) monothioglycerol,
   ii) L-cysteine,
   iii) thioglycolic acid; and
c) a pharmaceutically acceptable excipient.

The three antioxidants are uniquely effective for the claimed formulation. Surprisingly, common antioxidants, such as sodium metabisulfite, ascorbic acid, sodium EDTA, monoethanolamine gentisate, sodium formaldehyde sulfoxylate, sodium bisulfite, did not provide the desired formulation characteristics.

An especially preferred antioxidant is monothioglycerol.

The concentration of monothioglycerol is most preferably from about 1 part per million to 8.0 mg/ml, which concentration may be optimized for a given formulation based on the oxygen concentration contacting the formulation. The concentration of monothioglycerol may preferably be at least 0.6 mg/ml, more preferably at least 0.8 mg/ml, especially preferably is at least 1.0 mg/ml. The concentration of monothioglycerol is preferably up to 6 mg/ml, more preferably up to 5 mg/ml, and most preferably is up to 3 mg/ml.

It may be preferred that the concentration of monothioglycerol is from about 0.6 mg/ml to about 6 mg/ml. More preferably, the concentration of monothioglycerol is from about 0.8 mg/ml to about 5.0 mg/ml. It is especially preferred that the concentration of monothioglycerol is at least 1.0 mg./ml. An especially desired concentration is from 1.40 mg/ml to about 3.0 mg/ml. A further desired concentration is from about 2 mg/ml to about 3 mg/ml. A further preferred concentration of monothioglycerol is from about 1.2 mg/ml to about 2.4 mg/ml.

In general, the concentration of monothioglycerol, L-cysteine or Thioglycolic acid is most preferably from about 1 part per million to 8.0 mg/ml, which concentration may be optimized for a given formulation based on the oxygen concentration contacting the formulation. L-cysteine or thioglycolic acid are often most effective at a higher pH. It may be preferred that the concentration of monothioglycerol, L-cysteine or Thioglycolic acid is from about 1.0 mg/ml to about 6 mg/ml. More preferably, the concentration of monothioglycerol, L-cysteine or Thioglycolic acid is from about 0.8 mg/ml to about 5.0 mg/ml. It is especially preferred that the concentration of monothioglycerol, L-cysteine or Thioglycolic acid is at least 1.0 mg./ml. An especially desired concentration for monothioglycerol, L-cysteine or Thioglycolic acid is from 1.40 mg/ml to about 3.0 mg/ml. A further desired concentration is from about 2 mg/ml to about 3 mg/ml. A further preferred concentration of monothioglycerol, L-cysteine or Thioglycolic acid is from about 1.2 mg/ml to about 2.4 mg/ml. It is preferred to have a concentration of from about 0.1 (one tenth) mg/ml to 7 mg/ml. When the antioxidant is monothioglycerol or L-cycsteine, the preferred concentration range is from about 0.1 (one tenth)mg/ml to about 10.0 mg/ml.

The concentration of L-cysteine is preferably greater than 0.1 (one tenth) mg/ml, more preferably greater than 0.5 (one half) mg/ml and most preferably greater than 1 (one) mg/ml.

The concentration of L-cysteine is preferably less than 10 (ten) mg/ml, more preferably less than 8 (eight) mg/ml, and most preferably less than 6 (six) mg/ml.

The concentration of thioglycolic acid is preferably greater than 0.1 (one tenth) mg/ml, more preferably greater than 0.5 (one-half) mg/ml and most preferably greater than 1 (one) mg/ml.

The concentration of thioglycolic acid is preferably less than 10 (ten) mg/ml, more preferably less than 8 (eight) mg/ml, and most preferably less than 6 (six) mg/ml.

Additionally, combinations of the three antioxidants, selected from monothioglycerol, L-cysteine and thioglycerol, may also be used in this invention.

The concentration of pemetrexed is preferably from about 20 to about 100 mg/ml. It is especially preferred that the pemetrexed concentration is from about 30 mg/ml to about 70 mg/ml. A further preferred embodiment is when the pemetrexed concentration is from about 35 mg/ml to about 50 mg/ml. A further preferred embodiment is a pemetrexed concentration of from 38 mg/ml to about 44 mg/ml. An especially desired concentration of pemetrexed is about 40 mg/ml.

As used herein, the term "pemetrexed" refers to the stable salts, acids and free base forms thereof. The term includes, for example, the free acid, the pharmaceutically acceptable alkali metal, alkaline earth metal, non-toxic metal, ammonium, and substituted ammonium salts, such as for example, the sodium, potassium, lithium, calcium, magnesium, aluminum, zinc, ammonium, trimethylammonium, triethylammonium, monoethanolammonium, triethanolammonium, pyridinium, substituted pyridinium, and the like. The substituted ammonium salts are one especially preferred group of salts.

As used herein, the term "pharmaceutically acceptable excipient" means a pharmaceutically acceptable formulation carrier, solution or additive to enhance the formulation characteristics. Such additives are well known to the skilled artisan. While any pharmaceutically acceptable diluent is suitable, an especially preferred excipient for parenteral administration is saline solution. For example, sodium chloride, mannitol and the like.

The disodium salt of pemetrexed is particularly preferred for use in the present formulation.

The pH of the formulation is most preferably from about 5.5 to about 12. The formulation is more preferably from about pH 7 to about 11. It is especially desired that the pH of the formulation is from 8.0 to 9.0. It is further preferred that the pH is from about 8 to about 9 when the antioxidant is monothioglycerol. When the antioxidant is L-cysteine or thioglycolic acid or any salt form thereof, then the preferred pH is about 8 to about 10. The artisan will appreciate that combinations of these antioxidants can provide new preferred pH ranges. Standard modifications of the composition can provide compositions of various pH within the contemplation of this invention.

It is generally preferred that the process for preparing the formulation includes the use of a purge of an inert gas. Such inert gases are for example, nitrogen, argon, and the like. The use of an isolator to maintain low oxygen conditions is desirable, but not required for storage of the present formulation.

While any pharmaceutically acceptable stopper may be used to seal the vial containing the formulation, it is preferred to seal the vial with a stopper which is siliconized. A sterilized teflon coated stopper is desired for sealing the storage vial.

Most pharmaceutically acceptable liquid formulation vials or containers can be used to dispense the claimed formulation. It is desired that the containing vessel minimizes the concentration of oxygen that reaches the formulation. Thus, vials or ampules are especially desired vessels for the claimed formulation. A sealed vial is especially desired for commercial purposes in most countries.

The artisan will appreciate that the use of depyrogenated prewashed vials is desired for the storage of a sterile liquid formulation that is intended for parenteral use. The vial may be colored; however, a clear vial is acceptable for storage of the formulation. Any pharmaceutically acceptable material may be used to make the formulation container; however, glass is an especially preferred container material. A glass vial is a preferred container. Other packaging materials for parenterals like plastic vials are preferred options as well. For example, plastic vials may be useful.

It may be desirable to protect the bulk solution from light during the process of preparing the formulation; however, such protection is not required for the present formulation.

The resulting formulation can be sterlized using methods known to the artisan. Such sterilisation methods may include, for example, sterile filtration or heating. It is especially beneficial that the presently claimed formulation is stable during heat sterilization.

It is preferred that the headspace of the vial contains less than about 8% (eight percent) v/v Oxygen; however, the headspace of the vial may contain more than 8% oxygen if other conditions of the formulation are appropriately adjusted. It is more preferred that the headspace of the vial contains from about 2% to about 5% Oxygen. It is especially preferred that the headspace contains from about 3% to about 5% Oxygen. It is further preferred that the headspace contains less than about one (1) ppm oxygen. Also, preferred is when the headspace oxygen content is less than about 0.1% (one tenth percent) v/v oxygen. It is also a preferred condition that the headspace of the vial is less than about 1% (one percent) oxygen.

The headspace of the vial can be adjusted to minimize the formulation contact with oxygen. It is generally desired that the headspace is not more than about ⅓ (one third) of the total volume of the container, with the fill taking at least about ⅔ (two thirds) of the total volume of the container. For example, it may be preferred that 5 ml of fill be used for a 7.5 ml vial. If a greater headspace ratio to fill is desired, then the concentration of the antioxidant may be adjusted as necessary.

The pharmaceutical formulation provided herein is suitable for both human clinical use and veterinarian use for animals.

Pemetrexed can be prepared using the processes described in U.S. Pat. No. 5,473,071, hereby incorporated by reference in its entirety. Compositions of pemetrexed are useful to treat cancer, as described in the U.S. Pat. No. 5,344,932 patent as well as in Seminars in Oncology, Vol. 26, No. 2, Supplement 6 (April 1999).

Monothioglycerol is commercially available from suppliers of fine chemicals which are well known to the artisan. To further clarify, Monothioglycerol is Chemical Abstracts number: 96-27-5.

Likewise, L-cysteine (CAS: 52-90-4), L-cysteine hydrochloride monohydrate (CAS: 7048-04-6), L-cysteine hydrochloride monohydrate anhydrous (CAS: 52-89-1) and thioglycolic acid (CAS:68-11-1) are readily obtained from suppliers of fine chemicals.

DESCRIPTION OF PREFERRED EMBODIMENTS

The Present invention is seen more fully by the examples given below.

EXAMPLE 1

Pemetrexed, was prepared as a 40 mg/ml solution in water. Monothioglycerol was prepared as a 2.4 mg/ml solution using water for injection. The pH of the monothioglycerol solution was adjusted to 8.5 using sodium hydroxide.

The bulk solution was protected from light. The solution was purged with nitrogen for twenty minutes and then sterile filtered. The formulation was dispensed into prewashed, depyrogenated vials and then stoppered with a prewashed, presterilized teflon coated stopper. Caps were attached using a crimper. The sterile filtration and dispensing steps were conducted using a nitrogen isolator (5% v/v Oxygen).

The solution filled vials were heat sterilized.

EXAMPLE 2

A pharmaceutical composition was prepared substantially as described herein by Example 1, except that the antioxidant was 0.03% L-Cysteine and the pemetrexed concentration was four percent (4%).

EXAMPLE 3

A pharmaceutical composition was prepared substantially as described herein by Example 1, except that the antioxidant was 0.03% Thioglycolate and the pemetrexed concentration was four percent (4%).

We claim:

1. A pharmaceutical composition comprising:
   a) pemetrexed;
   b) at least one antioxidant selected from the group consisting of:
      c) monothioglycerol,
      ii) L-cysteine, and
      iii) thioglycolic acid; and
   c) a pharmaceutically acceptable excipient.

2. A pharmaceutical composition as claimed by claim 1 wherein the composition is a liquid formulation suitable for parenteral administration.

3. A pharmaceutical composition of claim 2 wherein pemetrexed is the disodium salt.

4. A pharmaceutical composition of claim 3 wherein the antioxidant is monothioglycerol.

5. A pharmaceutical composition of claim 4 wherein the monothioglycerol concentration is from about 1 (one) part per million to about 8 (eight) milligrams per milliliter.

6. A pharmaceutical composition of claim 5 wherein the monothioglycerol concentration is from about 1 (one) mg/ml to about 6 (six) mg/ml.

7. A pharmaceutical composition of claim 6 wherein the monothioglycerol concentration is from about 1 (one) mg/ml to about 2.5 (two and one half) mg/ml.

8. A pharmaceutical composition of claim 4 wherein the monothioglycerol concentration is from about 0.5 (one half) mg/ml to about 3 (three) mg/ml.

9. A pharmaceutical composition of claim 3 wherein the antioxidant is L-cysteine.

10. A pharmaceutical position of claim 9 wherein the L-cysteine concentration is from about 1 (one) part per million to about 8 (eight) mg/ml.

11. A pharmaceutical composition of claim 10 wherein the L-cysteine concentration is from about 1 (one) mg/ml to about 6 (six) mg/ml.

12. A pharmaceutical composition of claim 3 wherein the antioxidant is thioglycolic acid.

13. A pharmaceutical composition of claim 12 wherein the thioglycolic acid concentration is from about 1 (one) part per million to about 8 (eight) mg/ml.

14. A pharmaceutical composition of claim 13 wherein the thioglycolic acid concentration is from about 0.1 (one-tenth) mg/ml to about 6 (six) mg/ml.

15. A pharmaceutical composition of claim 4 wherein the monothioglycerol concentration is from about 0.1 (one tenth) mg/ml to about 10 (ten) mg/ml.

16. A pharmaceutical composition of claim 15 wherein the monothioglycerol concentration is from about 0.1 (one tenth) mg/ml to about 6 (six) mg/ml.

17. A pharmaceutical composition of claim 9 wherein the L-cysteine is from about 0.1 (one tenth) mg/ml to about 10 (ten) mg/ml.

18. A pharmaceutical composition of claim 17 wherein the L-cysteine is from about 0.1 (one tenth) mg/ml to about 6 (six) mg/ml.

19. A pharmaceutical composition of claim 12 wherein the thioglycolic acid is from about 0.1 (one tenth) mg/ml to about 10 (ten) mg/ml.

20. A pharmaceutical composition of claim 19 wherein the thioglycolic acid is from about 0.1 (one tenth) mg/ml to about 6 (six) mg/ml.

* * * * *

UNITED STATES PATENT AND TRADEMARK OFFICE
CERTIFICATE OF CORRECTION

PATENT NO.    : 6,686,365 B2
DATED         : February 3, 2004
INVENTOR(S)   : Bernd Ulrich Riebesehl and Jens Kemken It is certified that error appears in the above-identified patent and that said Letters Patent is hereby corrected as shown below:

<u>Column 6,</u>
Line 9, please delete the word "position" and replace it with -- composition --.

Signed and Sealed this

Fifteenth Day of June, 2004

JON W. DUDAS
*Acting Director of the United States Patent and Trademark Office*